United States Patent
Belk

(10) Patent No.: US 7,151,962 B2
(45) Date of Patent: Dec. 19, 2006

(54) METHOD AND APPARATUS TO CONTROL DELIVERY OF HIGH-VOLTAGE AND ANTI-TACHY PACING THERAPY IN AN IMPLANTABLE MEDICAL DEVICE

(75) Inventor: Paul A. Belk, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 293 days.

(21) Appl. No.: 10/835,451

(22) Filed: Apr. 29, 2004

(65) Prior Publication Data

US 2005/0245980 A1 Nov. 3, 2005

(51) Int. Cl.
*A61N 1/362* (2006.01)

(52) U.S. Cl. .................. 607/4; 607/5; 607/7; 607/9; 607/14

(58) Field of Classification Search ............. 607/4–5, 607/7, 34, 9, 14
See application file for complete search history.

(56) References Cited

U.S. PATENT DOCUMENTS

| | | | | |
|---|---|---|---|---|
| 4,407,288 A | 10/1983 | Langer et al. | ........ | 128/419 PG |
| 4,428,378 A | 1/1984 | Anderson et al. | ..... | 128/419 PG |
| 4,821,723 A | 4/1989 | Baker, Jr. et al. | ....... | 128/419 D |
| 4,865,036 A | 9/1989 | Chirife | .................... | 128/419 D |
| 4,949,719 A * | 8/1990 | Pless et al. | ..................... | 607/7 |
| 4,967,747 A | 11/1990 | Carroll et al. | ........... | 128/419 D |
| 5,176,137 A | 1/1993 | Erickson et al. | ........ | 128/419 D |
| 5,209,229 A | 5/1993 | Gilli | ........................ | 128/419 D |
| 5,251,624 A | 10/1993 | Bocek et al. | .................. | 607/6 |
| 5,318,591 A * | 6/1994 | Causey et al. | ................. | 607/5 |
| 5,330,505 A | 7/1994 | Cohen | .......................... | 607/6 |
| 5,458,619 A * | 10/1995 | Olson | ............................ | 607/4 |
| 5,662,688 A | 9/1997 | Haefner et al. | ................ | 607/5 |
| 5,713,924 A | 2/1998 | Min et al. | | |
| 5,855,593 A | 1/1999 | Olson et al. | .................... | 607/9 |
| 6,442,426 B1 * | 8/2002 | Kroll | ............................ | 607/4 |
| 6,718,204 B1 * | 4/2004 | DeGroot et al. | ............... | 607/4 |
| 6,892,094 B1 * | 5/2005 | Ousdigian et al. | ............ | 607/4 |
| 2003/0023273 A1 | 1/2003 | DeGroot et al. | | |

FOREIGN PATENT DOCUMENTS

| | | |
|---|---|---|
| EP | 0395242 | 10/1990 |
| EP | 0599588 | 6/1994 |
| EP | 1110581 | 6/2001 |
| WO | WO03/092792 | 11/2003 |

* cited by examiner

*Primary Examiner*—Robert Pezzuto
*Assistant Examiner*—Shevon Johnson
(74) *Attorney, Agent, or Firm*—Michael C Soldner; Girma Wolde-Michael

(57) ABSTRACT

A method and device for delivering a therapy in response to detection of abnormal cardiac rhythms that includes a first circuit delivering a first therapy and a second circuit delivering a second therapy, the second circuit including an energy storage device for storing energy associated with the second therapy and a charging circuit selectively coupled to the storage device to generate the stored energy. A control circuit controls the first circuit and the second circuit to deliver the first therapy substantially simultaneous with the charging of the energy storage device in response to the predetermined event being detected, and decouples the energy storage device from the charging circuit during a redetect period subsequent to delivery of the first therapy. The control circuit recouples the energy storage device and the charging circuit in response to the microprocessor detecting the predetermined event during the redetect period.

30 Claims, 10 Drawing Sheets

METHOD AND APPARATUS TO CONTROL DELIVERY OF HIGH-VOLTAGE AND ANTI-TACHY PACING THERAPY IN AN IMPLANTABLE MEDICAL DEVICE

FIELD OF THE INVENTION

The present invention relates generally to implantable medical devices; and, more particularly, to reducing power consumption in an implantable medical device.

BACKGROUND OF THE INVENTION

Implantable cardioverter-defibrillator (ICD) art has long distinguished ventricular tachyarrhythmias by rate and type. Ventricular tachycardias (VTs), which generally include arrhythmias having rates between 150 and 250 bpm or more, can be further differentiated by their ECG configuration as either monomorphic or polymorphic. Arrhythmias with rates above an upper VT range, and up to approximately 350 bpm, are often termed ventricular flutter waves. Chaotic waveforms at rates higher than 350 bpm are classified as ventricular fibrillation (VF).

To treat each type of arrhythmia with an appropriate therapy, ICDs have been equipped with "tiered therapies". Such devices are generally referred to as Pacer-Cardioverter-Defibrillators (PCDs). PCDs generally differentiate arrhythmias by rates, with programmable therapies to treat a respective type of detected arrhythmia(s). In such devices, the less-dangerous arrhythmias such as VT are treated by delivering a series of low-power pacing pulses to the heart at a relatively high rate. This therapy is often referred to as anti-tachyarrhythmia pacing therapy (ATP). In contrast, more perilous arrhythmias such as VF are often treated using a more aggressive shock therapy. For example, many PCDs may be programmed to first treat a VT with low-power ATP and then, if the VT progresses to ventricular flutter or fibrillation, deliver one or more high-power cardioversion or defibrillation shocks.

Many implantable anti-tachycardia pacemakers have the capability of providing a variety of anti-tachycardia pacing regimens. Normally, these regimens are applied according to a pre-programmed sequence, such as burst or ramp therapies among others. Each therapy extends over a series of a predetermined number of pacing pulses. After the series of pacing pulses is delivered, the devices check to determine whether the series of pulses was effective in terminating the detected tachyarrhythmia. Termination is generally confirmed by a return to sinus rhythm, for example, identified by a sequence of a predetermined number of spontaneous depolarizations separated by greater than a defined interval. In the absence of detected termination, the PCD applies more aggressive therapies such as synchronized cardioversion shocks or defibrillation shocks. While the delivery of ATP in some cases makes shock therapy unnecessary, a further reduction in the frequency of shock delivery is still desirable.

Applying an electrical pulse to the heart, whether a pacing pulse or a shock, requires charging of one or more output capacitors. Generally, the amount of energy required to delivery pacing pulses is low. This type of therapy may therefore be delivered by a low-power output circuit relatively instantaneously. On the other hand, high-power shocks require a set of high-voltage capacitors that may require several seconds to reach a fully-programmed charge. As stated above, when a tiered therapy approach is utilized, both of these therapies may be used to "break" the tachyarrhythmia. That is, first ATP is delivered. During this time, the high-voltage capacitors may be charged so that if ATP fails to break the VT, a high-voltage shock may be delivered soon thereafter. If the VT is terminated by ATP, the charged high-voltage capacitors must abort delivery and internally "leak off" the stored energy in the capacitors, which depletes battery power. This can significantly shorten the useful life of the implanted device.

What is needed, therefore, is a method and apparatus to deliver successful ATP therapy without needlessly depleting battery resources.

BRIEF DESCRIPTION OF THE DRAWINGS

Aspects of the present invention will be readily appreciated as they become better understood by reference to the following detailed description when considered in connection with the accompanying drawings, wherein.

DETAILED DESCRIPTION OF THE DRAWINGS

Figure 1:
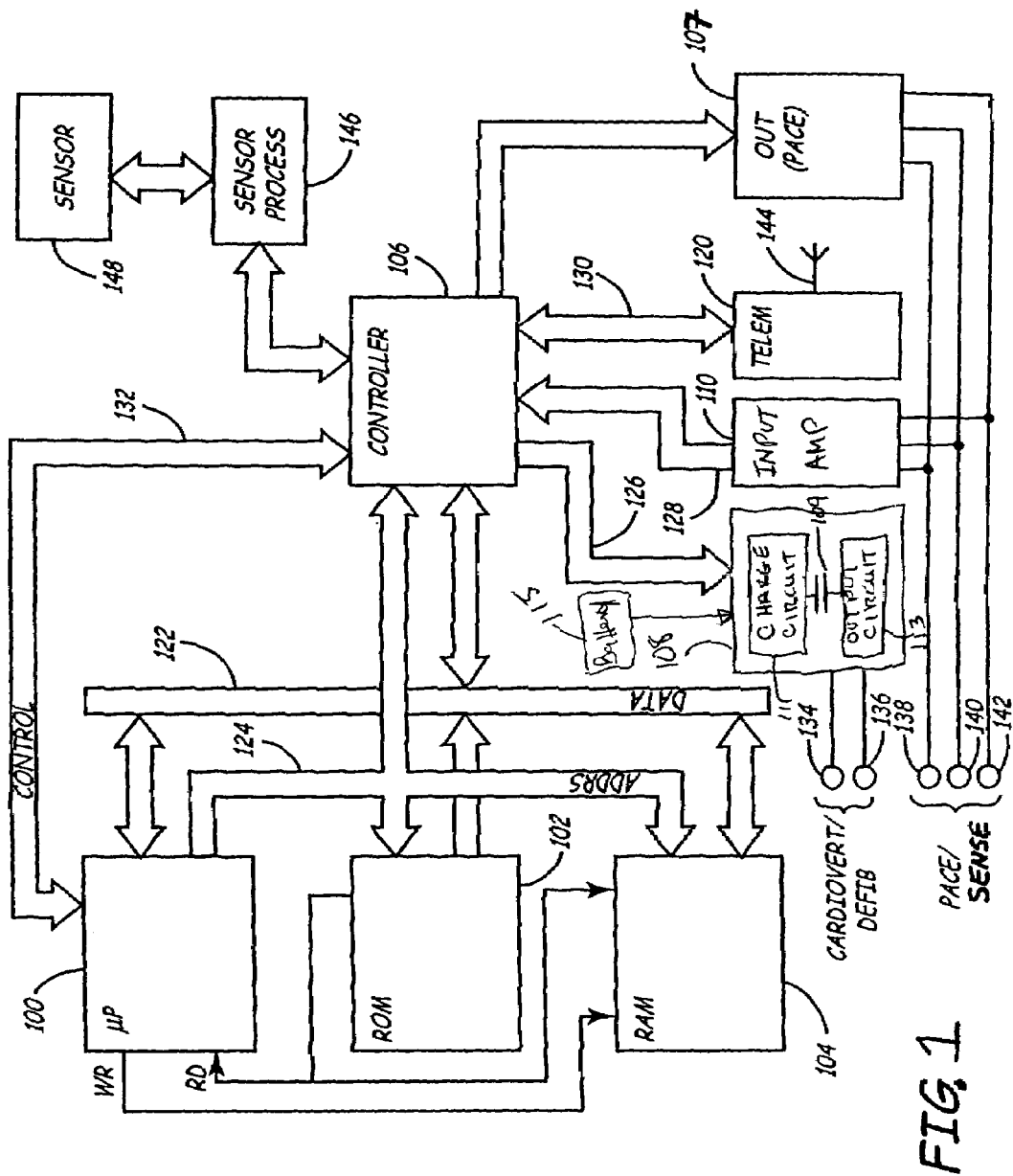
FIG. 1 is a block diagram of an illustrative embodiment of an implantable medical device in which the present invention may be employed.

FIG. 1 is a block diagram of an illustrative embodiment of an implantable medical device in which the present invention may be employed. As illustrated in FIG. 1, the device is embodied as a microprocessor based stimulator. However, other digital circuitry embodiments and analog circuitry embodiments are also believed to be within the scope of the invention. For example, devices having general structures as illustrated in U.S. Pat. No. 5,251,624 issued to Bocek et al., U.S. Pat. No. 5,209,229 issued to Gilli, U.S. Pat. No. 4,407,288, issued to Langer et al, U.S. Pat. No. 5,662,688, issued to Haefner et al., U.S. Pat. No. 5,855,593, issued to Olson et al., U.S. Pat. No. 4,821,723, issued to Baker et al. or U.S. Pat. No. 4,967,747, issued to Carroll et al., all incorporated herein by reference in their entireties, may also be usefully employed in conjunction with the present invention. Similarly, while the device of FIG. 1 takes the form of a ventricular pacemaker/cardioverter, the present invention may also be usefully employed in a device having atrial pacing and cardioversion capabilities. FIG. 1 should thus be considered illustrative, rather than limiting with regard to the scope of the invention.

The primary elements of the implantable medical device illustrated in FIG. 1 are a microprocessor 100, read-only memory (ROM) 102, random-access memory (RAM) 104, a digital controller 106, an input amplifier circuit 110, two output circuits 108 and 107, and a telemetry/programming unit 120. Read-only memory 102 stores the basic programming for the device, including the primary instruction set defining the computations performed to derive the various timing intervals employed by the cardioverter. RAM 104 generally serves to store variable control parameters, such as programmed pacing rate, programmed cardioversion intervals, pulse widths, pulse amplitudes, and so forth which are programmed into the device by the physician. Random-access memory 104 also stores derived values, such as the stored time intervals separating tachyarrhythmia pulses and the corresponding high-rate pacing interval.

Controller 106 performs all of the basic control and timing functions of the device. Controller 106 includes at least one programmable timing counter, which is initiated upon detection of a ventricular activation, and which times intervals thereafter. This counter is used to generate the basic timing intervals used to deliver anti-tachy pacing (ATP) pulses, and to measure other intervals used within the context of the current invention. On time-out of the pacing escape interval or in response to a determination that a cardioversion or defibrillation pulse is to be delivered, controller 106 triggers the appropriate output pulse from high-voltage output stage 108, as discussed below.

Following generation of stimulus pulses, controller 106 may be utilized to generate corresponding interrupts on control bus 132, waking microprocessor 100 from its "sleep" state, allowing microprocessor 100 to perform any required mathematical calculations, including all operations associated with evaluation of return cycle times and selection of anti-tachyarrhythmia therapies according to the present invention. The timing/counter circuit in controller 106 also controls timing intervals such as ventricular refractory periods, as is known in the art. The time intervals may be determined by programmable values stored in RAM 104, or values stored in ROM.

Controller 106 also generates interrupts for microprocessor 100 on the occurrence of sensed ventricular depolarizations or beats. On occurrence of a sensed ventricular depolarization, in addition to an interrupt indicating its occurrence placed on control bus 132, the then-current value of the timing/counter within controller 106 is placed onto data bus 122. This value may be used by microprocessor 100 in determining whether a tachyarrhythmia is present, and further, in determining the intervals separating individual tachyarrhythmia beats.

Output stage 108 contains a high-output pulse generator capable of generating shock therapy to be applied to the patient's heart via electrodes 134 and 136, which are typically large surface area electrodes mounted on or in the heart, or located subcutaneously. Other electrode configurations may also be used, including two or more electrodes arranged within and around the heart. Typically the high output pulse generator includes one or more high-voltage capacitors 109, a charging circuit 111 for transferring energy stored in a battery 115 to the high-voltage capacitors 109, an output circuit 113 and a set of switches (not shown) to allow delivery of monophasic or biphasic cardioversion or defibrillation pulses to the electrodes employed.

In addition to output circuit 108, output circuit 107 is provided to generate pacing pulses. This circuit contains a pacing pulse generator circuit that is coupled to electrodes 138, 140 and 142, and which are employed to accomplish cardiac pacing, including ATP pacing pulses, by delivery of a electrical stimulation between electrode 138 and one of electrodes 140 and 142. Electrode 138 is typically located on the distal end of an endocardial lead, and is typically placed in the apex of the right ventricle. Electrode 140 is typically an indifferent electrode mounted on, or adjacent to, the housing of the cardioverter defibrillator. Electrode 142 may be a ring or coil electrode located on an endocardial lead slightly proximal to the tip electrode 138, or it may be another electrode positioned inside or outside the heart. Although three electrodes 138–142 are shown in FIG. 1 for delivering pacing pulses, it is understood that the present invention may be practiced using any number of electrodes positioned in any pacing electrode configuration known in the art. Output circuit 108 may be controlled by control bus 126, which allows the controller 106 to determine the time, amplitude and pulse width of the pulse to be delivered. This circuit may also determine which electrode pair will be employed to deliver the pulse.

Sensing of ventricular depolarizations (beats) is accomplished by input amplifier 110, which is coupled to electrode 138 and one of electrodes 140 and 142. Signals indicating both the occurrence of natural ventricular beats and paced ventricular beats are provided to the controller 106 via bus 128. Controller 106 passes data indicative of the occurrence of such ventricular beats to microprocessor 100 via control bus 132 in the form of interrupts, which serve to wake up microprocessor 100. This allows the microprocessor to perform any necessary calculations or to update values stored in RAM 104.

Optionally included in the device is one or more physiologic sensors 148, which may be any of the various known sensors for use in conjunction with implantable stimulators. For example, sensor 148 may be a hemodynamic sensor such as an impedance sensor as disclosed in U.S. Pat. No. 4,865,036, issued to Chirife or a pressure sensor as disclosed in U.S. Pat. No. 5,330,505, issued to Cohen, both of which are incorporated herein by reference in their entireties. Alternatively, sensor 148 may be a demand sensor for measuring cardiac output parameters, such as an oxygen saturation sensor disclosed in U.S. Pat. No. 5,176,137, issued to Erickson et al. or a physical activity sensor as disclosed in U.S. Pat. No. 4,428,378, issued to Anderson et al., both of which are incorporated herein by reference in their entireties. Sensor processing circuitry 146 transforms the sensor output into digitized values for use in conjunction with detection and treatment of arrhythmias.

External control of the implanted cardioverter/defibrillator is accomplished via telemetry/control block 120 that controls communication between the implanted cardioverter/pacemaker and an external device, such as a communication network or an external programmer, for example. Any conventional programming/telemetry circuitry is believed workable in the context of the present invention. Information entering the cardioverter/pacemaker from the programmer is passed to controller 106 via bus 130. Similarly, information from the cardioverter/pacemaker is provided to the telemetry block 120 via bus 130.

Figure 2A:
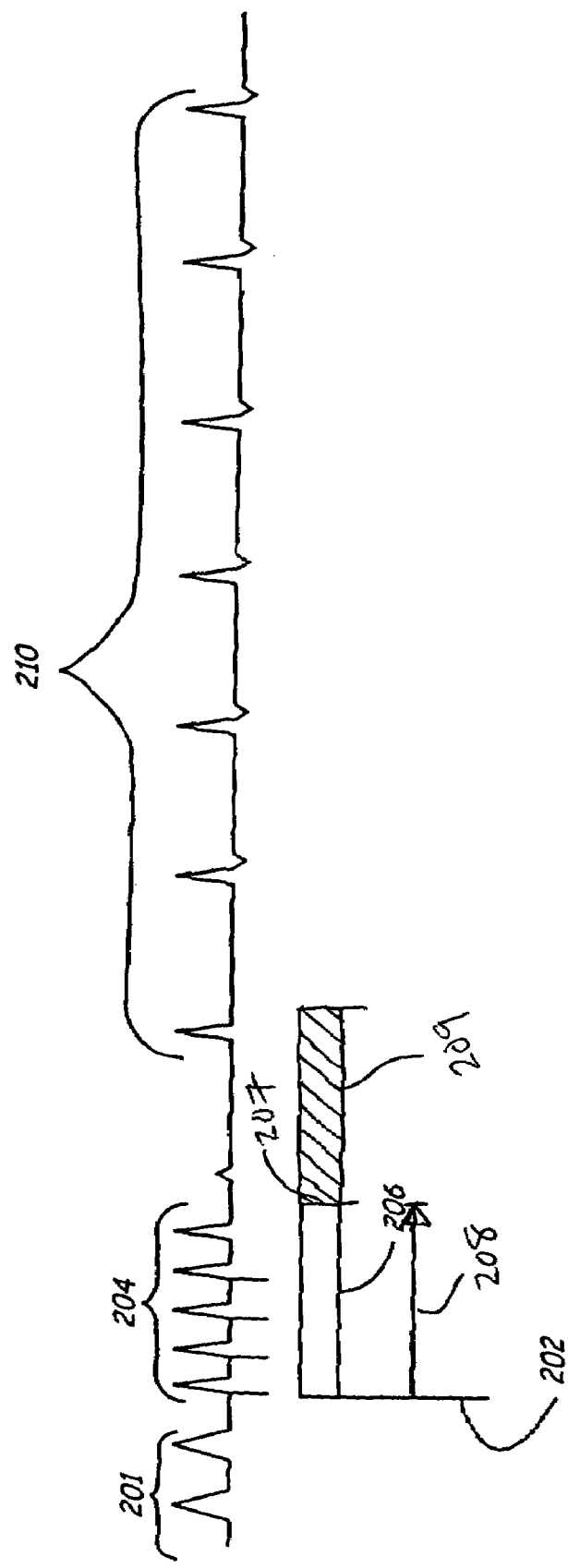
FIGS. 2A and 2B are exemplary timing diagrams illustrating an anti-tachyarrhythmia pacing therapy during capacitor charging (ATP-DCC) mode of an implantable medical device according to the present invention.
Figure 2B:
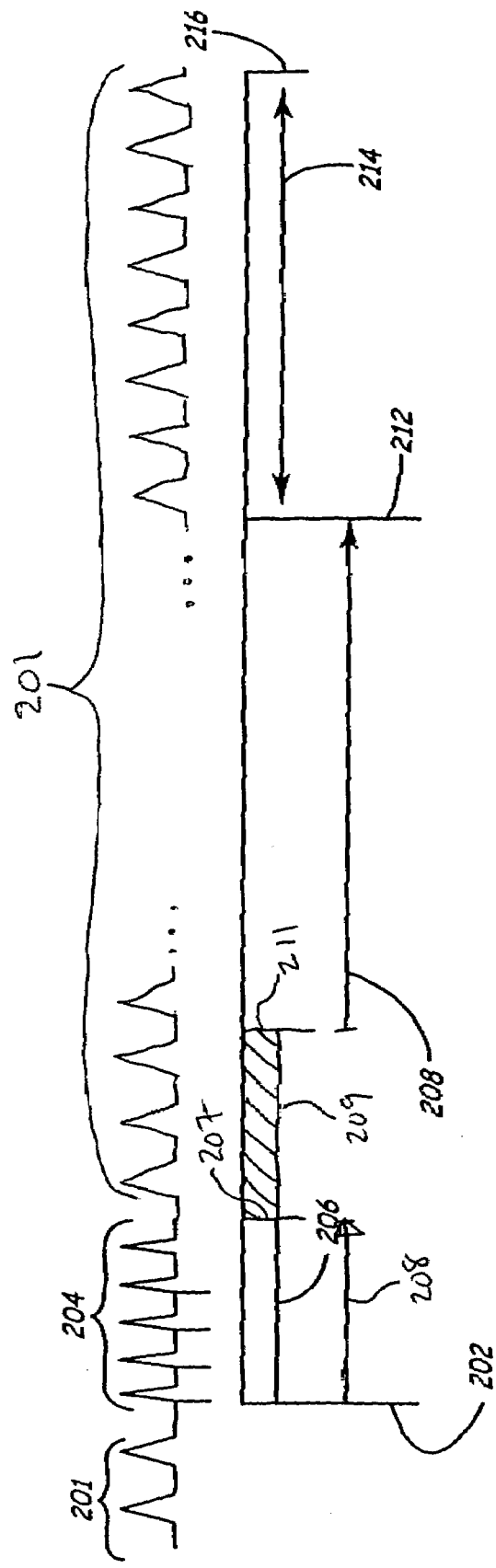

FIGS. 2A and 2B are exemplary timing diagrams illustrating an anti-tachyarrhythmia pacing therapy during capacitor charging (ATP-DCC) mode of an implantable medical device according to the present invention. As illustrated in FIG. 2A, after detection of a VT cardiac rhythm 201, microprocessor 100 activates controller 106 to initiate both capacitor charging 208 of high voltage capacitor or capacitors 109 via charging circuit 111 and ATP therapy delivery 204 substantially simultaneously at time 202. High-rate VT 201, which in one embodiment is defined to include rhythms between 185 and 260 beats per minute (bpm), is treated by one sequence of Burst or Ramp or other type ATP-DCC therapy 204 that extend until an end 207 of a predetermined period of time 206, or alternatively, for a predetermined number of pacing pulses ending at end time 207. Once delivery of the sequence of ATP-DCC therapy is completed, i.e., at end 207 of predetermined period of time 206, capacitor charging 208 is paused during a redetection or verification period 209 during which a determination is made as to whether the VT rhythm 201 is redetected. In this case, the sequence of ATP-DCC therapy causes the VT rhythm to terminate, or "break", so that a normal sinus rhythm 210 is resumed. Therefore, capacitor charging 208 remains in a paused state until VT cardiac rhythm 201 is redetected, as will be described in detail below.

As illustrated in FIG. 2B, if VT rhythm 201 is redetected during period 209, capacitor charging 208 is resumed once period 209 is completed, i.e., at an end time 211 of time period 209. According to one embodiment of the present invention, a second sequence of ATP-DCC therapy may be delivered substantially simultaneously with the resumption of capacitor charging 208 at end time 211 and the process repeated until capacitor 109 is completely charged, as will be described in detail below. According to another embodiment of the present invention, illustrated in FIG. 2B, no additional ATP-DCC therapy is delivered and resumption of capacitor charging 208 continues until capacitors 109 are charged to a desired charge level at charge time end 212 in preparation for delivery of a shock, if necessary. A non-committed synchronization period 214 begins at charge time end 212. During this synchronization period 214, the patient's cardiac rhythm is evaluated to locate an appropriate time to deliver a shock and to determine if the VT rhythm is redetected. The shock will be delivered at the end 216 of the synchronization period 214 unless it is determined that the VT episode has terminated. If the episode has terminated prior to the end 216 of the synchronization period 214, the process charge remains on the capacitors 109 and the device continues to monitor for subsequent detected VT rhythms, at which point the process is repeated.

Figure 3:
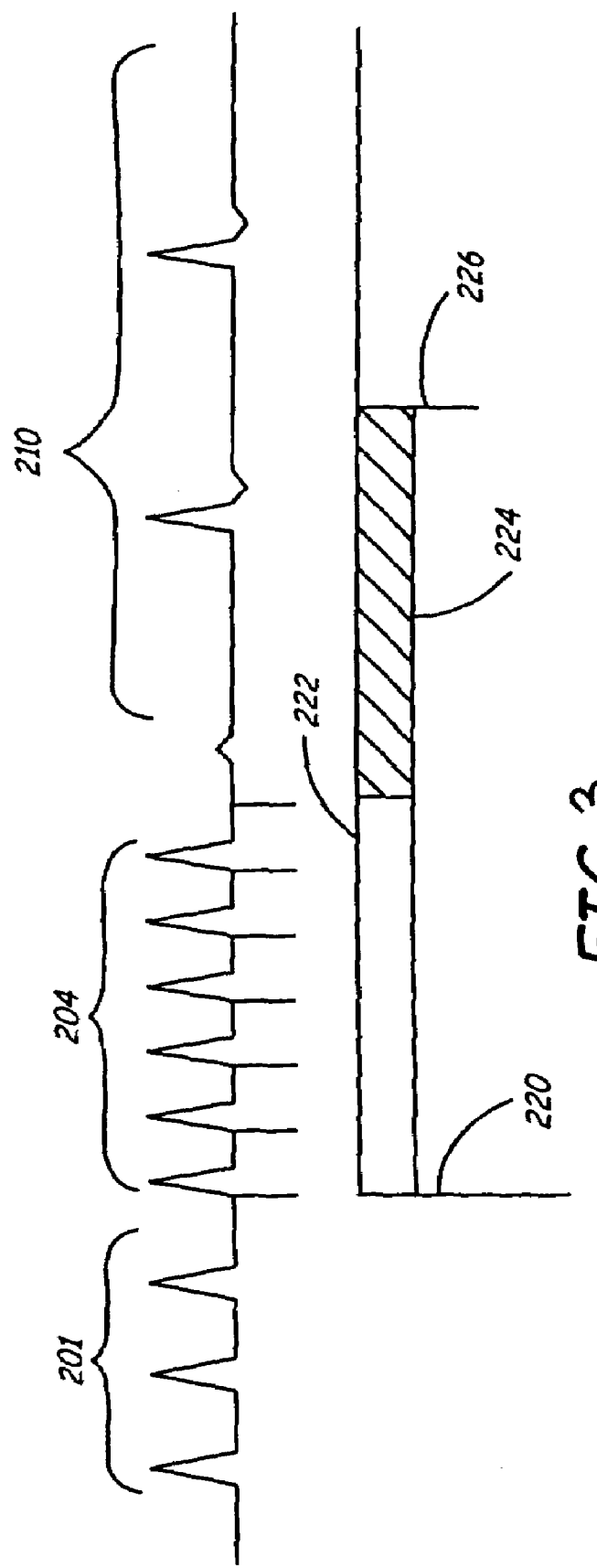
FIG. 3 is an exemplary timing diagram illustrating an anti-tachyarrhythmia pacing therapy before capacitor charging (ATP-BCC) mode of an implantable medical device according to the present invention.

FIG. 3 is an exemplary timing diagram illustrating an anti-tachyarrhythmia pacing therapy before capacitor charging (ATP-BCC) mode of an implantable medical device according to the present invention. As illustrated in FIG. 3, delivery of ATP therapy 204 is initiated at time 220 following detection of a VT episode 201 and continues through a corresponding delivery time 222. In the example illustrated in FIG. 3, ATP therapy returns the patient to normal sinus rhythm 210. The ICD device detects the break in VT by the change in cardiac rate as well as the return to normal sinus rhythm 210 during a redetection or verification period 224. As a result, no charging of the high-voltage capacitors is initiated at time 226. However, if the ATP-BCC therapy does not return the patient to normal sinus rhythm and the VT episode 201 is redetected during verification period 224, another sequence of ATP therapy is initiated simultaneously with charging of the capacitors 109, as illustrated in FIG. 4, and described below.

According to the current invention, operation of the ICD may transition from ATP-DCC mode shown in FIGS. 2A and 2B to execution in ATP-BCC mode shown in FIG. 3 based on programmable criteria. In one embodiment, this "Charge Saver" function switches the ICD device operation from ATP-DCC to ATP-BCC mode after attaining a user-programmed consecutive number of ATP successes since the previous follow-up session. ATP therapy is generally considered successful when the VT breaks/aborts prior to shock delivery, although other criteria may be defined for determining the success of the ATP therapy. The device will revert back to ATP-DCC mode following a predetermined criteria, which may include a predetermined number of failures to break a VT in the ATP-BCC operational mode, as will be discussed further in reference to FIG. 4.

Figure 4:
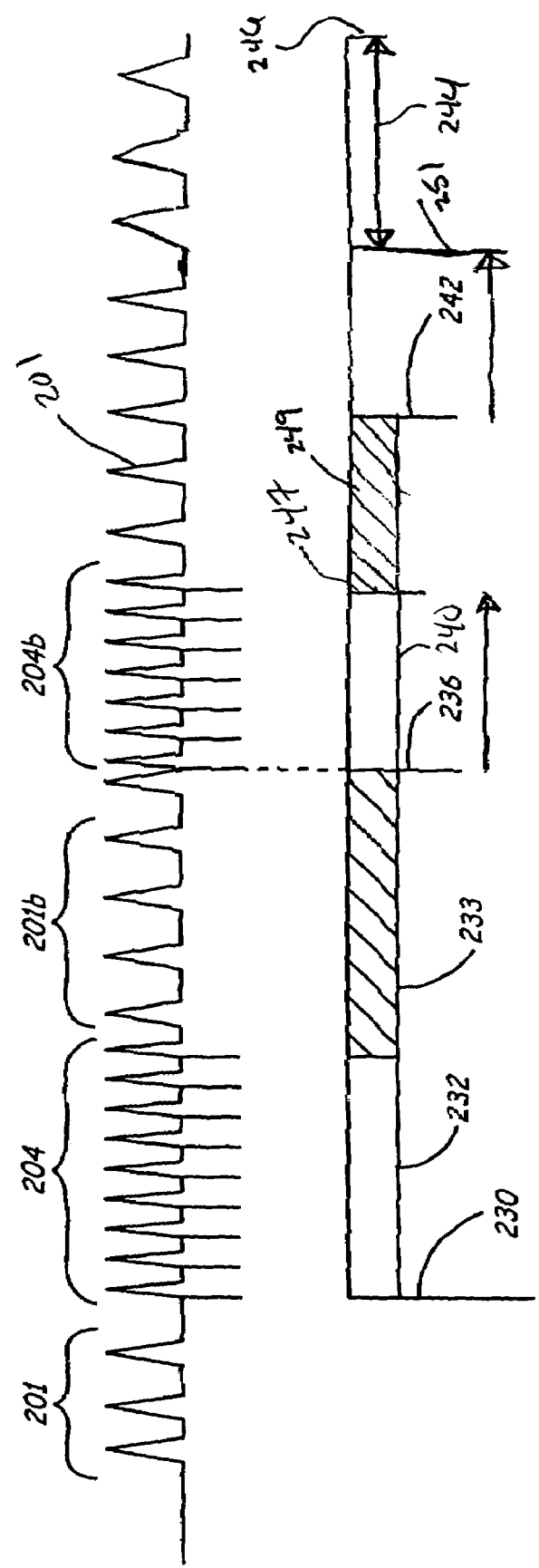
FIG. 4 is an exemplary timing diagram illustrating an ongoing VT episode that fails to break following ATP-BCC therapy.

FIG. 4 is an exemplary timing diagram illustrating an ongoing VT episode that fails to break following ATP-BCC therapy. As illustrated in FIG. 4, ATP-BCC therapy 204 is delivered during delivery time 232 following VT detection 201. Thereafter, verification period 233 confirms the ongoing VT episode 201b. According to an embodiment of the present invention, once it is determined that the initial sequence of ATP-BCC therapy 204 was not successful at terminating the VT episode, i.e., at time 236, a second sequence of ATP therapy 204b is delivered over a time period 240 coinciding with charging of capacitors 236, with both capacitor charging 238 and ATP therapy delivery 204b beginning substantially simultaneously at time 236. Studies such as the Medtronic PainFREE $R_x$ study have shown that this additional ATP sequence has a low likelihood of accelerating the ventricular rate, and in fact, has the potential for terminating a VT episode.

Once delivery of subsequent ATP therapy 204b is completed, i.e., at end time 247 of time period 240, capacitor charging 238 is paused, and a determination is made as to whether the VT rhythm 201 is redetected during a redetection or verification period 249 during which a determination is made as to whether the VT rhythm 201 is redetected. If, as illustrated in FIG. 4, VT rhythm 201 is redetected during period 249, capacitor charging 238 is resumed once redetection or verification period 249 is completed, i.e., at end time 242.

According to one embodiment of the present invention, a second sequence of ATP-DCC therapy may be delivered substantially simultaneously with the resumption of capacitor charging 238 at end time 242 and the process is repeated until capacitor 109 is completely charged, as will be described in detail below. According to another embodiment of the present invention, illustrated in FIG. 4, no additional ATP-DCC therapy is delivered and resumption of capacitor charging 238 continues until capacitors 109 are charged to a desired charge level at charge time end 251 in preparation for delivery of a shock, if necessary. A non-committed synchronization period 244 begins once capacitors 109 are charged to the desired charge level at charge time end 251. During this synchronization period 244, the patient's cardiac rhythm is evaluated to locate an appropriate time to deliver a shock and to determine if the VT rhythm is redetected. The shock will be delivered at an end 246 of the synchronization period 244 unless it is determined during resynchronization period 244 that the VT episode has terminated. If the episode is determined to have terminated during synchronization period 244, the process charge remains on the capacitors 109 and the device continues to monitor for subsequent detected VT rhythms.

According to another aspect of the present invention, if a predetermined number of episodes of VT are not terminated by ATP-BCC therapy such that shock delivery occurs as shown in FIG. 4, the system reverts from ATP-BCC mode to the ATP-DCC mode.

Figure 5:
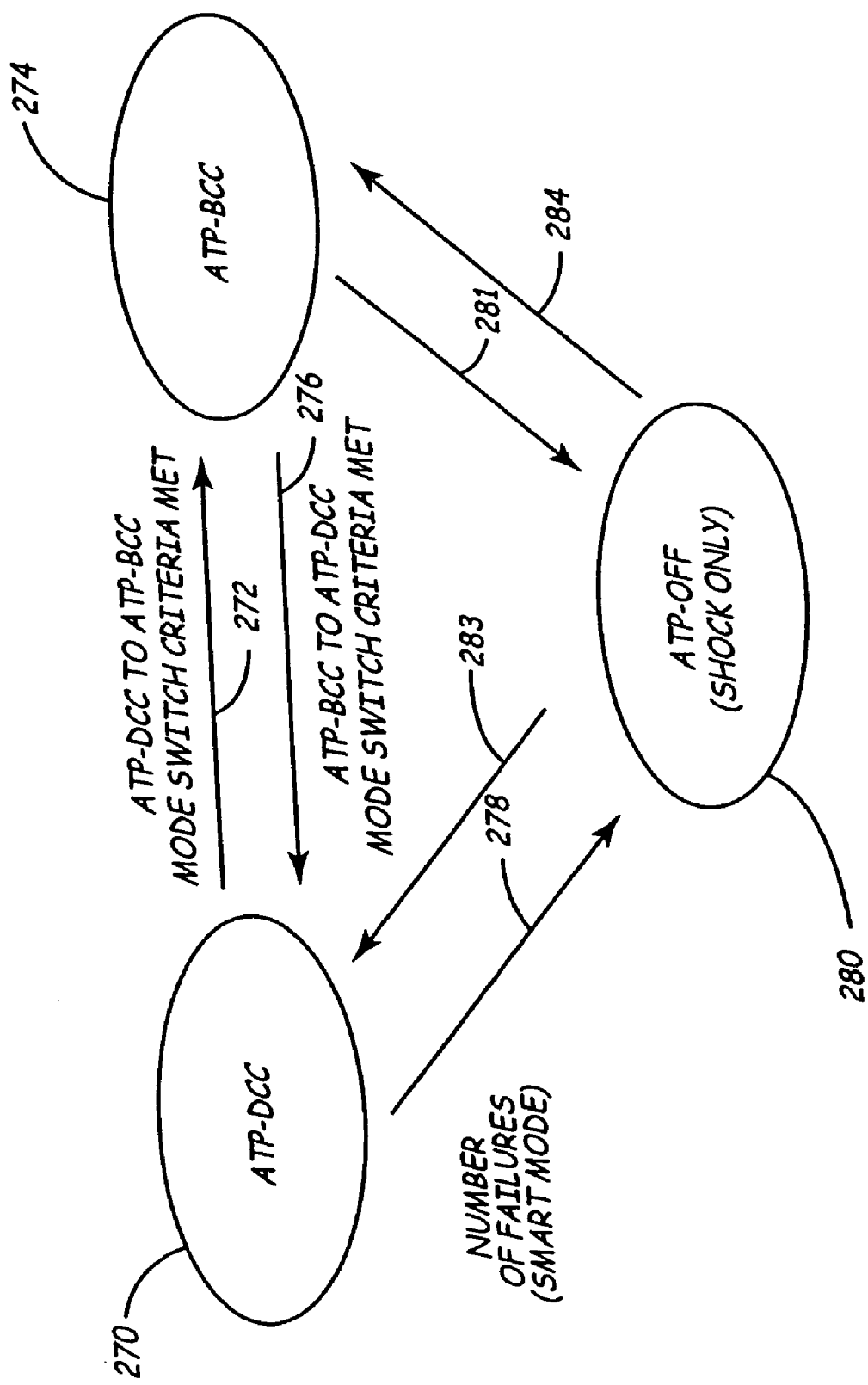
FIG. 5 is a state diagram illustrating transitions between therapy modes, according to the present invention.

FIG. 5 is a state diagram illustrating transitions between therapy modes, according to the present invention. ICD devices are shipped from the factory with ATP-DCC mode and the Charge Saver feature enabled, as illustrated by state 270 as well as the Charge Saver feature. At the time of implant, the physician may choose whether to disable the Charge Saver feature. In one embodiment of the invention, other programmable parameters may be selected by the physician if the Charge Saver feature is enabled. These parameters may include the number of successful ATP-DCC therapy sessions that must be delivered prior to the automated activation of ATP-BCC mode, as will be discussed further below. It is understood that the ICD device could be shipped with the ATP-DCC mode and the Charge Saver feature disabled so that the physician chooses whether to enable the features at the time of implant.

During operation with Charge Saver enabled and the system operating in ATP-DCC, a transition to ATP-BCC mode shown as state 274 may be triggered by the delivery of a predetermined number X of ATP-DCC therapy sessions that succeed in breaking the VT rhythm. This transition is depicted by arrow 272. Conversely, when operating in ATP-BCC mode and after a predetermined number Y of failed ATP-BCC therapy attempts, the system transitions to ATP-DCC mode as shown by arrow 276. As discussed above, in one embodiment of the invention, X and Y are programmable. Alternatively, these numbers may be predetermined, non-programmable values. Finally, these numbers may represent consecutive ATP therapy sessions, or may involve a set of "S of T" therapy sessions. For example, a transition from ATP-DCC to ATP-BCC may be selected to occur if 4 of 5 ATP-DCC therapy sessions are determined to be successful.

Other trigger criteria may be used instead of, or in addition to, the above criteria to initiate a switch between ATP-DCC and ATP-BCC modes. In one embodiment, the system stores both cycle length (CL) and/or R-wave morphology of a VT rhythm to determine whether the type of VT currently being experienced is the same type of VT that occurred during a recently-detected episode or episodes. This is important since patients can exhibit different types of VT, each of which may respond differently to ATP therapy. If the characteristics of the current episode are the same as the previous episode, and the previous episode responded favorably to ATP-BCC therapy, the device remains in the ATP-BCC mode of operation upon detection of a break in rate. On the other hand, if the CL and/or R-wave morphology has changed, the system may be programmed to revert back to the ATP-DCC mode of operation.

According to the foregoing embodiment, different mode transition criteria may be specified for each type of VT rhythm. For example, a transition from ATP-DCC to ATP-BCC therapy may be triggered by M consecutive successful therapy sessions for a first type of VT. This same mode transition may be triggered by M' of N successful therapy sessions for a second type of VT. This allows therapies to be individually selected for different types of VT rhythms.

In yet another embodiment, the system mode-switching criteria takes into account VT frequency. As discussed above, some patients experience "VT storms" involving the occurrence of a large number of episodes within a short period of time, such as hours or even minutes. Such episodes, which usually involve VT rhythms having similar CLs and morphologies, may significantly impact battery resources. In this embodiment, the occurrence of a predetermined number of VT episodes in a predetermined time period may trigger a switch from ATP-DCC to ATP-BCC mode to save battery resources.

According to an alternative embodiment of the invention, a programmable threshold duration is used to detect VT storms. If two consecutive VT episodes occur within this predefined threshold duration, a count is incremented. If the count reaches a predetermined value within some larger programmable time period, a mode switch may be triggered. Once a mode switch to ATP-BCC mode occurs, continued operation in ATP-BCC mode may be predicated on obtaining a predetermined success rate using any of the mechanisms discussed above. Alternatively, another threshold time can be defined to track episode frequency in the ATP-BCC mode such that if the inter-episode duration exceeds this value, a transition back to ATP-DCC mode occurs.

If desired, waveform morphology criteria may be applied to VT storm detection. For example, VT episodes that are separated by longer periods of time such as weeks or months may involve different types of VT rhythms. Therefore, for all VT episodes, or just the VT episodes separated by a predetermined time period, mode-switch criteria may be individually specified for respective types of VT rhythms as discussed above.

Transition from ATP-DCC to ATP-BCC mode or vice versa could also be predicated on the length of an episode. For example, the episode length measured from first detection to the termination of a rhythm could be used as the mode-switching criteria. In one embodiment, longer episodes could trigger a transition to ATP-DCC mode.

According to yet another aspect of the invention, the detection of VT storms may trigger a patient alert (audible, vibratory or other). For example, the patient may be notified to contact a physician so that operating parameters of the system may be re-evaluated, and mode-switching conditions may be re-programmed, if necessary.

Another aspect of the invention relates to an optional programmable feature for disabling all modes of ATP. If this "Smart Mode" feature is enabled and a predetermined criteria is met, all ATP therapy is disabled. In one embodiment, this Smart Mode feature operates when execution is occurring in ATP-DCC mode and a predetermined number of failed therapy attempts is detected. This transition is shown by arrow 278 and state 280. The number of failed therapy attempts needed to trigger this transition may be programmable, or may be a predetermined number which is preferably "four". Thereafter, the ICD device will only deliver the programmed shock therapy. In another embodiment, this feature could also be provided when execution is occurring in ATP-BCC mode, as shown by arrow 281. In yet another embodiment, the switch from either ATP-BCC or ATP-DCC mode could be triggered by a VT rhythm or waveform morphology that meets a predetermined criteria. For instance, the transition to a mode wherein ATP is disabled may be triggered by detection of a fast VT rhythm that exceeds 250 bpm.

In one embodiment, after a transition occurs to a mode wherein ATP is disabled, shock therapy will continue until intervention is provided to re-activate the ATP-DCC mode. Such intervention may be provided, for example, during a subsequent follow-up session. In another embodiment, the system will continue operation in this mode until a defined criteria is met. For example, if the transition to the ATP-disabled mode occurs because of a fast VT rhythm, the system will revert back to the previous mode of operation after the fast VT episode has been terminated by the shock delivery, as shown by arrows 283 and 284.

Figure 6A:
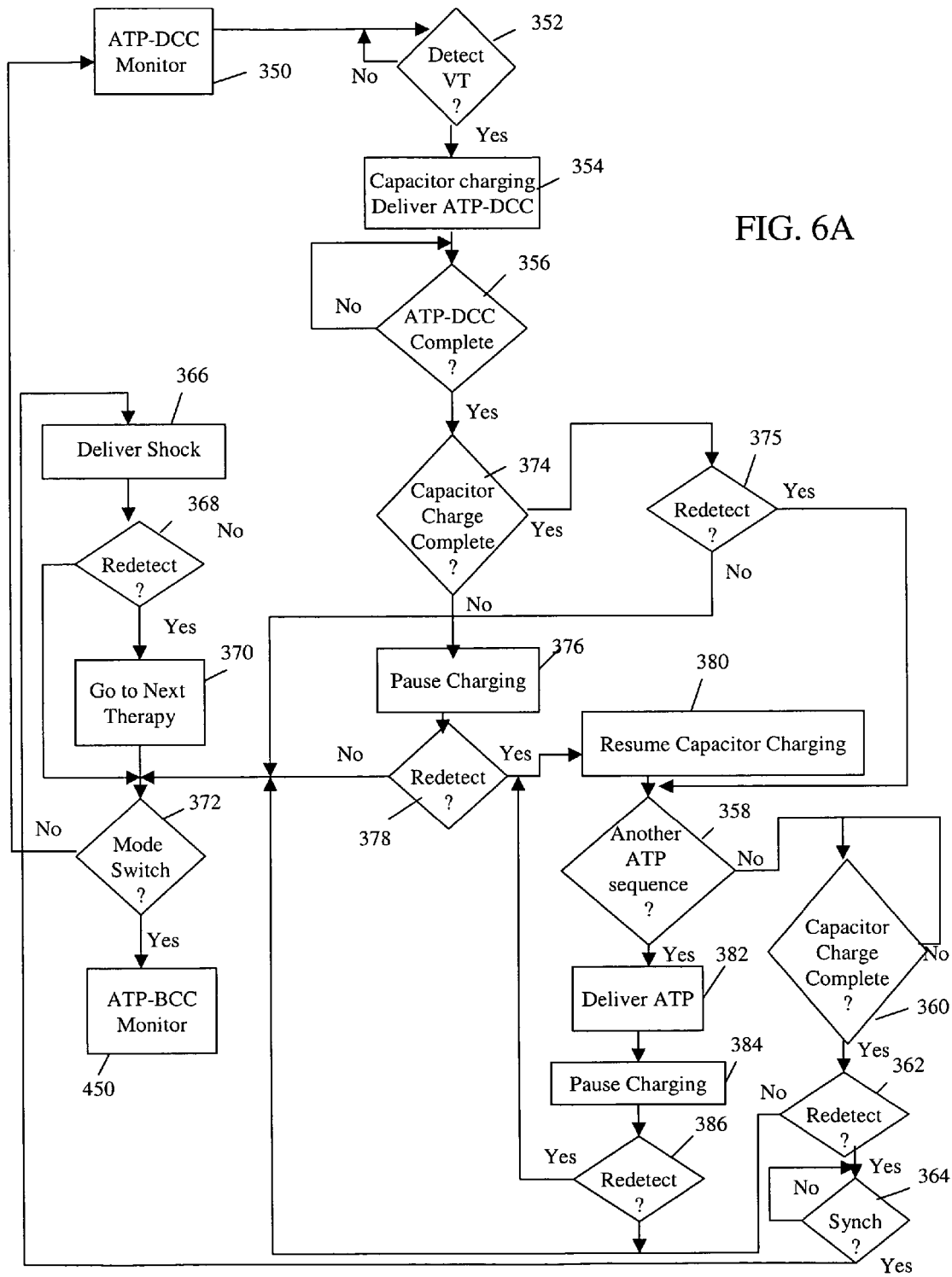
FIG. 6A is a flowchart of operation of an implantable medical device in an ATP-DCC mode, according to an embodiment of the present invention.

FIG. 6A is a flowchart of operation of an implantable medical device in an ATP-DCC mode, according to an embodiment of the present invention. As illustrated in FIG. 6A, an implantable medical device such as the one shown in FIG. 1 is generally implanted with the ATP-DCC mode enabled, although it maybe implanted with ATP-BCC mode enabled, if desired. While in the nominal ATP-DCC mode, block 350, the device continuously monitors for the presence of tachyarrhythmias. Once a VT rhythm is detected, block 352, for example, delivery of an initial ATP-DCC therapy sequence and charging of the high-voltage capacitors are initiated substantially simultaneously, block 354. After delivery of the initial ATP-DCC therapy sequence is completed, YES in block 356, a determination is made as to whether charging of the capacitors 109 is completed to a desired level, block 374.

If the capacitors 109 are not yet charged to the desired charge level, NO in block 374, charging of the capacitors 109 is paused, block 376, and a determination is made as to whether the initially delivered ATP sequence was successful at terminating the VT rhythm, block 378. If the initial ATP sequence was successful at terminating the VT rhythm and the rhythm is not redetected, NO in block 378, a determination is made as to whether the device should transition from the ATP-DCC mode to the ATP-BCC mode, block 372, based on the factors described above in reference to FIG. 5. If it is determined that the device should not transition from the ATP-DCC mode to the ATP-BCC mode, NO in block 372, the process returns to block 352 to monitor for subsequent detected VT rhythms, at which point the process is repeated. If a mode switch is indicated, YES in block 372, the device transitions to the ATP-BCC mode, block 450, which is described below in reference to FIG. 6B.

If the initially ATP sequence was not successful at terminating the VT rhythm and the rhythm is redetected, YES in block 378, charging of the capacitors 109 is resumed, block 380, and a determination is made as to whether another, ATP sequence should be initiated prior to delivering of shock therapy, block 358.

According to the present invention, the number of ATP sequences that are delivered prior to delivering shock therapy is programmable, and can include only one initial sequence, or a multiple number of sequences, such as three for example. The number chosen may be dependent upon many factors or combination of factors, such as the rate of the detected rhythm, whether the detected rhythm is a stable rhythm, or whether the detected rhythm is part of a cluster of detected rhythms that occur in a specified period of time.

If the programmed number of ATP sequences have been delivered, NO in block 358, and capacitors 109 are charged to the desired charge level, YES in block 360, a non-committed synchronization period begins during which the patient's cardiac rhythm is evaluated to locate an appropriate time to deliver a shock, block 364, and to determine if the VT rhythm is redetected, block 362. The shock will be delivered, block 366, at an end of the synchronization period unless it is determined that the VT episode has terminated, i.e., is no longer detected, NO in block 362.

If the episode is no longer detected, NO in block 362, the determination is made as to whether the device should transition from the ATP-DCC mode to the ATP-BCC mode, block 372, based on the factors described above in reference to FIG. 5. If it is determined that the device should not transition from the ATP-DCC mode to the ATP-BCC mode, NO in block 372, the process returns to block 352 to monitor for subsequent detected VT rhythms, at which point the process is repeated. If a mode switch is indicated, YES in block 372, the device transitions to the ATP-BCC mode, block 450, which is described below in reference to FIG. 6B.

Once the synchronization period is completed, YES in block 364, the shock is delivered, block 366. Upon completion of delivery of the shock therapy, a determination is made as to whether the VT rhythm was terminated by the delivered shock, block 368. Several criteria may be used to make this determination, including cardiac rate, cycle length, R-wave morphology, and/or any other criteria known in the art for this purpose. If the VT has not terminated, the device begins the process of delivering a next programmed therapy in a tiered therapy approach, assuming a tiered therapy approach is utilized, block 370. Once all of the programmed therapies have been exhausted in block 370, or in the case where a tiered approach is not utilized after the shock was delivered in block 366, or if the VT rhythm is not redetected after delivery of the shock NO in block 368, the determination is made as to whether the device should transition from the ATP-DCC mode to the ATP-BCC mode, block 372, based on the factors described above in reference to FIG. 5. If it is determined that the device should not transition from the ATP-DCC mode to the ATP-BCC mode, NO in block 372, the process returns to block 352 to monitor for subsequent detected VT rhythms, at which point the process is repeated. If a mode switch is indicated, YES in block 372, the device transitions to the ATP-BCC mode, block 450, which is described below in reference to FIG. 6B.

If it is determined that all of the predetermined number of ATP therapy sequences have not been delivered, i.e., another ATP sequence should be delivered prior to delivering shock therapy, YES in block 358, the subsequent sequence of ATP therapy is delivered, block 382. Once delivery of the subsequent ATP therapy has completed, charging of capacitors 109 is paused, block 384, and a determination is made as to whether the subsequent delivered ATP sequence was successful at terminating the VT rhythm, block 386. If the VT rhythm was not terminated and is redetected, YES in block 386, charging of capacitors 109 is resumed, block 380, and the above-described process of determining whether the programmed number of ATP sequences have been delivered, block 358, is repeated.

If the VT rhythm was terminated as a result of the last delivered ATP sequence and is not redetected, NO in block 386, the determination is made as to whether the device should transition from the ATP-DCC mode to the ATP-BCC mode, block 372, based on the factors described above in reference to FIG. 5. If it is determined that the device should not transition from the ATP-DCC mode to the ATP-BCC mode, NO in block 372, the process returns to block 352 to monitor for subsequent detected VT rhythms, at which point the process is repeated. If a mode switch is indicated, YES in block 372, the device transitions to the ATP-BCC mode, block 450, which is described below in reference to FIG. 6B.

If capacitors 109 are determined to be charged to a desired charge level once delivery of the initial ATP-DCC therapy sequence is completed, YES in block 374, a determination is made as to whether the delivered initial ATP-DCC therapy sequence was successful at terminating the VT rhythm, block 375. If the initial ATP-DCC therapy sequence was successful at terminating the VT rhythm and therefore the rhythm is not redetected, NO in block 375, the determination is made as to whether the device should transition from the ATP-DCC mode to the ATP-BCC mode, block 372, based on the factors described above in reference to FIG. 5. If it is determined that the device should not transition from the ATP-DCC mode to the ATP-BCC mode, NO in block 372, the process returns to block 352 to monitor for subsequent detected VT rhythms, at which point the process is repeated. If a mode switch is indicated, YES in block 372, the device transitions to the ATP-BCC mode, block 450, which is described below in reference to FIG. 6B.

If capacitor charging has completed and the initial ATP-DCC therapy sequence was not successful at terminating the VT rhythm and therefore the rhythm redetected, YES in blocks 374 and 375, the above-described process of determining whether the programmed number of ATP sequences have been delivered, block 358, described above, is repeated, and is therefore omitted for the sake of brevity.

Figure 6B:
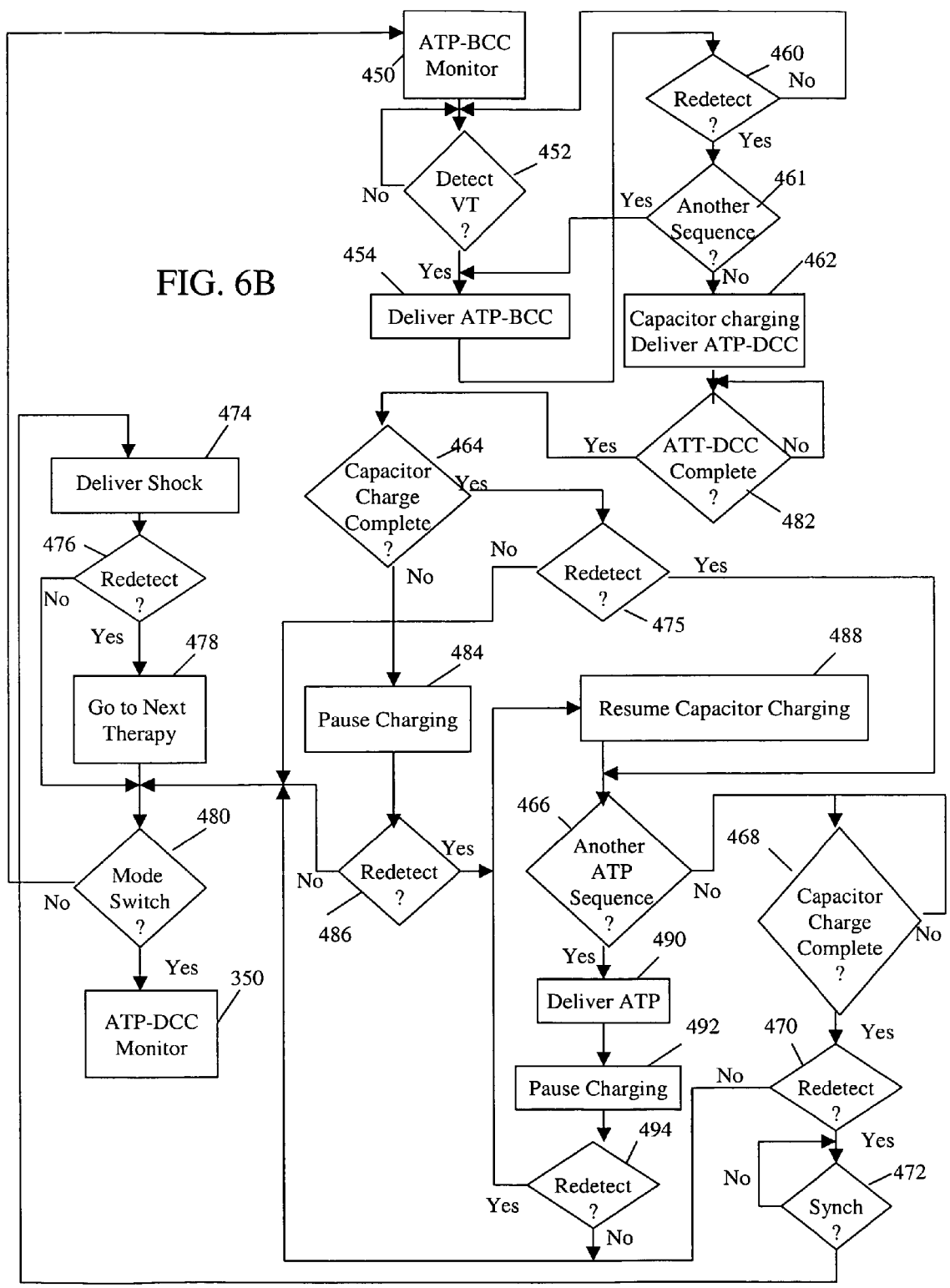
FIG. 6B is a flowchart of operation of an implantable medical device in an ATP-BCC mode, according to an embodiment of the present invention.

FIG. 6B is a flowchart of operation of an implantable medical device in an ATP-BCC mode, according to an embodiment of the present invention. As illustrated in FIG. 6B, when in the ATP-BCC mode state of operation, block 450, the device monitors for the presence of tachyarrhythmias, block 452. When a tachyarrhythmia meets VT criteria, for example, YES in block 452, an ATP-BCC therapy sequence is initiated without initiating charging of the capacitors 109, block 454. Once delivery of the ATP-BCC therapy sequence has completed, a determination is made as to whether the delivered ATP-DCC therapy sequence was successful at terminating the VT rhythm, block 460. If ATP-BCC therapy has successfully terminated the VT rhythm, NO in block 460, the system reverts to the nominal state illustrated in block 450.

If the ATP-BCC therapy was not successful and the VT episode is redetected and meets VT criteria, YES in block 460, a determination is made as to whether another sequence of the ATP-BCC therapy should be delivered, block 461. According to the present invention, the number of ATP sequences that may be delivered prior to initiating the charging of high voltage capacitors and delivery of the ATP-DCC therapy of block 462 is programmable, and can include only a single sequence, or a multiple number of sequences, such as three for example. The number chosen may be dependent upon many factors or combination of factors, such as the rate of the detected rhythm, whether the detected rhythm is a stable rhythm, or whether the detected rhythm is part of a cluster of detected rhythms that occur in a specified period of time.

Once the programmed number of ATP-BCC sequences have been delivered, NO in block 461, delivery of an ATP-DCC therapy sequence and charging of the high-voltage capacitors are initiated substantially simultaneously, block 462. After delivery of the initial ATP-DCC therapy sequence has completed, YES in block 482, a determination is made as to whether charging of the capacitors is completed to a desired level, block 464. If capacitors 109 are not yet charged to a desired charge level, NO in block 464, charging of the capacitors 109 is paused, block 484, and a determination is made as to whether the initially delivered ATP sequence was successful at terminating the VT rhythm, block 486.

If the initially delivered ATP sequence was successful and therefore the episode is no longer detected, NO in block 486, a determination is made as to whether the device should transition from the ATP-BCC mode to the ATP-DCC mode, block 480, based on the factors described above in reference to FIG. 5. If it is determined that the device should not transition from the ATP-BCC mode to the ATP-DCC mode, NO in block 480, the process returns to block 452 to monitor for subsequent detected VT rhythms, at which point the process is repeated. If a mode switch is indicated, YES in block 480, the device transitions to the ATP-DCC mode, block 350, which is described above in reference to FIG. 6A.

If the initially delivered ATP sequence was not successful and therefore the episode is redetected, YES in block 486, charging of the capacitors is resumed, block 488, and a determination is made as to whether another ATP sequence should be initiated prior to delivering of shock therapy, block 466. According to the present invention, the number of subsequent ATP sequences that may be delivered after delivery of the initial sequence and prior to delivering the shock therapy is programmable, and can include only a single additional sequence, or a multiple number of sequences. The number chosen may be dependent upon many factors or combination of factors, such as the rate of the detected rhythm, whether the detected rhythm is a stable rhythm, or whether the detected rhythm is part of a cluster of detected rhythms that occur in a specified period of time.

Once a subsequent ATP-DCC sequence is delivered, block 490, charging of capacitors 109 is paused, block 492, and a determination is made as to whether the subsequent delivered ATP sequence or sequences was successful at terminating the VT rhythm, block 494. If the VT rhythm was not terminated and is redetected, YES in block 494, charging of capacitors 109 is resumed, block 488, and the above-described process of determining whether another ATP sequences should be delivered, block 466, is repeated. If the VT rhythm is terminated by the subsequent delivered ATP sequence and therefore is not redetected, NO in block 494, the determination is made as to whether the device should transition from the ATP-BCC mode to the ATP-DCC mode, block 480, based on the factors described above in reference to FIG. 5. If it is determined that the device should not transition from the ATP-BCC mode to the ATP-DCC mode, NO in block 480, the process returns to block 452 to monitor for subsequent detected VT rhythms, at which point the process is repeated. If a mode switch is indicated, YES in block 480, the device transitions to the ATP-DCC mode, block 350, which is described above in reference to FIG. 6A.

Once the programmed number of ATP sequences have been delivered, NO in block 466, and capacitors 109 are charged to the desired charge level, YES in block 468, the non-committed synchronization period begins during which the patient's cardiac rhythm is evaluated to locate an appropriate time to deliver a shock, block 472, and to determine if the VT rhythm is redetected, block 470. The shock will be delivered, block 474, at an end of the synchronization period unless it is determined that the VT episode has terminated and is no longer detected, NO in block 470. If the episode is no longer detected, a determination is made as to whether the device should transition from the ATP-BCC mode to the ATP-DCC mode, block 480, based on the factors described above in reference to FIG. 5. If it is determined that the device should not transition from the ATP-BCC mode to the ATP-DCC mode, NO in block 480, the process returns to block 452 to monitor for subsequent detected VT rhythms, at which point the process is repeated. If a mode switch is indicated, YES in block 480, the device transitions to the ATP-DCC mode, block 350, which is described above in reference to FIG. 6A.

After the shock has been delivered in block 474, a determination is made as to whether the VT rhythm was terminated by the delivered shock, block 476. Several criteria may be used to make this determination, including cardiac rate, cycle length, R-wave morphology, and/or any other criteria known in the art for this purpose. If the VT rhythm has not terminated, the device begins the process of delivering a next programmed therapy in a tiered therapy approach, assuming a tiered therapy approach is utilized, block 478. Once all of the programmed therapies have been exhausted in block 478, or in the case where a tiered approach is not utilized, once the shock is delivered in block 474, or if the VT rhythm is no longer detected after delivery of the shock, NO in block 476, a determination is made as to whether the device should transition from the ATP-BCC mode to the ATP-DCC mode, block 480, based on the factors described above in reference to FIG. 5. If it is determined that the device should not transition from the ATP-BCC mode to the ATP-DCC mode, NO in block 480, the process returns to block 452 to monitor for subsequent detected VT rhythms, at which point the process is repeated. If a mode switch is indicated, YES in block 480, the device transitions to the ATP-DCC mode, block 350, which is described above in reference to FIG. 6A.

If capacitors 109 are determined to be charged to a desired charge level once delivery of the initial ATP-DCC therapy sequence is completed, YES in block 464, a determination is made as to whether the delivered initial ATP-DCC therapy sequence was successful at terminating the VT rhythm, block 475. If the initial ATP-DCC therapy sequence was successful at terminating the VT rhythm and therefore the rhythm is not redetected, NO in block 475, the determination is made as to whether the device should transition from the ATP-DCC mode to the ATP-BCC mode, block 480, based on the factors described above in reference to FIG. 5. If it is determined that the device should not transition from the ATP-DCC mode to the ATP-BCC mode, NO in block 480, the process returns to block 452 to monitor for subsequent detected VT rhythms, at which point the process is repeated. If a mode switch is indicated, YES in block 480, the device transitions to the ATP-DCC mode, block 350, which is described below in reference to FIG. 6A.

If capacitor charging has completed and the initial ATP-DCC therapy sequence was not successful at terminating the VT rhythm and therefore the rhythm is redetected, YES in blocks 464 and 475, the above-described process of determining whether the programmed number of ATP sequences have been delivered, block 466, described above, is repeated, and is therefore omitted for the sake of brevity.

Figure 7:
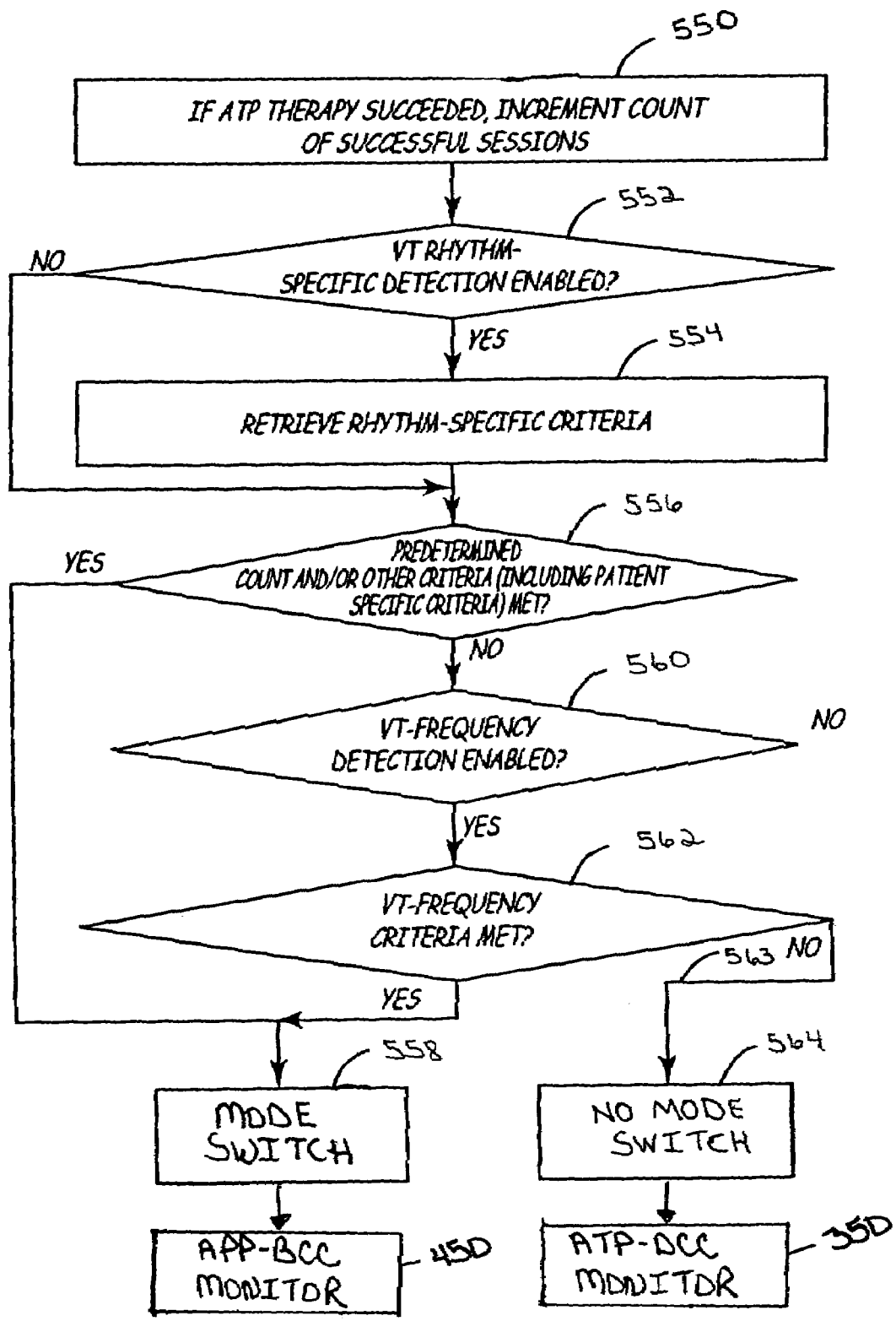
FIG. 7 is a flowchart illustrating a mode switch according to an embodiment of the present invention.

FIG. 7 is a flowchart illustrating a mode switch according to an embodiment of the present invention. As illustrated in FIG. 7, in order to determine whether to transition from the ATP-DCC mode to the ATP-BCC mode in block 372 of FIG. 6A, a count of successful ATP therapy sessions is incremented each time the most-recently provided ATP therapy terminates the VT rhythm, block 550. A determination is then made as to whether rhythm-specific criteria will be used to make the mode-switch determination, block 552. As described above, it may be desirable to define specific criteria for the various types of VT rhythms, as may be identified by cycle length, and waveform morphology.

If rhythm-specific criteria will be utilized, the VT rhythm associated with the most recent VT episode is analyzed, and the corresponding criteria retrieved, as shown in block 554. Otherwise, the standard criterion is utilized. This criterion may be programmable, or a pre-set value.

After the criterion is selected, if necessary, the count of successful ATP therapy sessions is compared against the appropriate criteria in block 556 to determine whether a mode switch should be performed. It may be noted that this criteria may involve a consecutive number of successes, a predetermined number of successes in a predetermined period of time, or may instead require X of Y successes, as discussed above. Other criteria that do, or do not, involve a count of successful therapy-delivery sessions may be used instead of, or in addition to, the predetermined count criteria. For example, the duration of a VT episode may be utilized to trigger a mode switch to ATP-BCC mode, if desired. As will be discussed further below, this criteria may include patient-specific criteria. If the pre-defined criteria are met, the mode switch from the ATP-DCC mode, block 350, to the ATP-BCC mode, block 450, is performed, block 558.

If the predetermined criteria are not met in decision block 556, a determination is made as to whether VT-frequency monitoring is enabled, block 560 so that VT storms may be detected. If VT-frequency monitoring is enabled, a determination is made as to whether the VT-frequency criteria are met, block 562. This involves making a determination as to whether a predetermined number of VT episodes are detected in a specific period of time. Alternatively, an inter-episode threshold duration may be defined to detect VT storms in the manner discussed above. The detection may also take into consideration types of VT episodes, if desired. For example, separate running counts may be maintained for various types of VT episodes, with the types being determined by CL and waveform morphology. Each type of episode may also be associated with different criteria in a manner similar to that discussed. For example, a VT storm indication may be met if a first type of VT episode occurs X times in Y minutes, whereas a VT storm indication is met for a second type of VT episode occurring X' times in Y' minutes, and so on.

If any of the one or more VT-frequency criteria is met, a mode switch from ATP-DCC therapy mode to ATP-BCC therapy mode occurs, block 558, and processing continues in ATP-BCC mode, block 450 of FIG. 6B. Otherwise, if VT-frequency detection is not enabled, or the VT-frequency criteria are not met, no mode switch occurs, block 564, and processing continues in ATP-DCC mode, block 350 of FIG. 6A.

Figure 8:
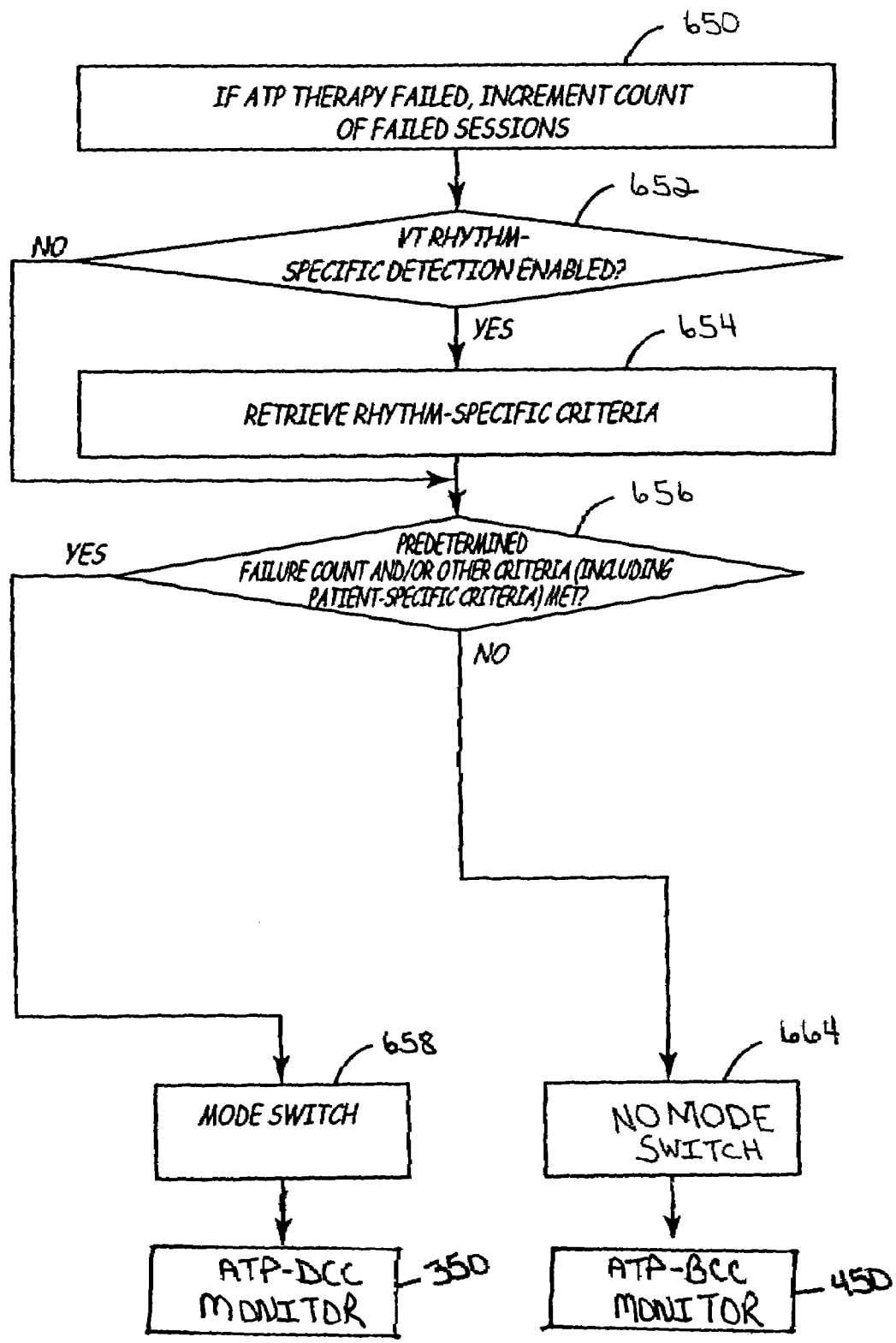
FIG. 8 is a flowchart illustrating a mode switch according to an embodiment of the present invention.

FIG. 8 is a flowchart illustrating a mode switch according to an embodiment of the present invention. As illustrated in FIG. 8, in order to determine whether to transition from the ATP-BCC mode to the ATP-DCC mode in block 480 of FIG. 6B, a count of unsuccessful ATP therapy sessions is incremented each time that the most-recently provided ATP therapy fails to terminate the VT rhythm, block 650. A determination is then made as to whether rhythm-specific criteria will be used to make the mode-switch determination, block 652. As described above, different criteria may be defined for different VT rhythms.

If rhythm-specific criteria will be utilized, the VT rhythm associated with the most recent VT episode is analyzed, and the corresponding criteria retrieved, as shown in block 654. Such rhythm-specific criteria may involve a mode switch from ATP-BCC to ATP-DCC mode based on the detection of a particular type of VT episode, for instance. In another instance, the rhythm-specific criteria may involve a count of a number of failed therapy attempts, for example.

If rhythm-specific criteria are not to be utilized as determined in block 652, a standard criterion may be utilized. In either case, the appropriate criteria are used in block 656 to determine whether a mode switch from the ATP-BCC therapy mode to the ATP-DCC therapy mode should be performed. It may be noted that this criteria may involve a consecutive number of failed therapy attempts, may instead require X of Y failed therapy attempts, or may require a predetermined number of failures in a predetermined amount of time as discussed above. In one embodiment, a predetermined number of failed therapy attempts from the last patient medical check-up may be utilized as the trigger criteria. In another embodiment, the criteria may alternatively or additionally include conditions unrelated to failed therapy attempts, such as the occurrence of a particular type of rhythm, or a specific change in a type of rhythm, as noted above. This criteria may also include patient-specific conditions related to patient medical history. If this criteria is met, YES in block 656, the mode switch is performed, block 658, and processing continues in ATP-DCC therapy mode, block 350 of FIG. 6A. If the criteria are not met, no mode switch is performed, block 564, and processing continues in the ATP-BCC therapy mode, block 450 of FIG. 6B.

As discussed above, many different types of criteria may be used to trigger a mode switch. In one embodiment, this criteria is programmable, and may be initially programmed and/or thereafter altered based on patient history. This allows system operation to be tailored for each patient. This could take into account, for example, a patient's individual response to ATP therapies. Programming can be accomplished, for example, using telemetry systems known in the art.

Some of the techniques described above may be embodied as a computer-readable medium comprising instructions for a programmable processor such as microprocessor 100 or control circuitry 106 shown in FIG. 1. The programmable processor may include one or more individual processors, which may act independently or in concert. A "computer-readable medium" includes but is not limited to any type of computer memory such as floppy disks, conventional hard disks, CR-ROMS, Flash ROMS, nonvolatile ROMS, RAM and a magnetic or optical storage medium. The medium may include instructions for causing a processor to perform any of the features described above for initiating a session of the escape rate variation according to the present invention.

The preceding specific embodiments are illustrative of the practice of the invention. It is to be understood, therefore, that other expedients known to those of skill in the art or disclosed herein may be employed without departing from the invention or the scope of the appended claim. It is therefore to be understood that the invention may be practiced otherwise than as specifically described, without departing from the scope of the present invention. As to every element, it may be replaced by any one of infinite equivalent alternatives, only some of which are disclosed in the specification.

What is claimed is:

1. An implantable medical device, comprising:
   an input circuit sensing cardiac signals;
   a microprocessor detecting a predetermined event in response to the sensed signals;
   a first circuit delivering a first therapy;
   a second circuit for delivering a second therapy, the second circuit including an energy storage device to store energy associated with the second therapy and a charging circuit selectively coupled to the storage device to transfer a predetermined level of the stored energy to the charging circuit; and
   a control circuit controlling the first circuit and the second circuit to deliver the first therapy substantially simultaneous with coupling of the charging circuit and the energy storage device in response to the predetermined event being detected, and decoupling the energy storage device and the charging circuit during a redetect period subsequent to delivery of the first therapy and prior to the predetermined level of the stored enemy being transferred to the charging circuit, wherein the control circuit recouples the energy storage device and the charging circuit in response to the microprocessor detecting the predetermined event during the redetect period.

2. The device of claim 1, wherein delivery of the first therapy corresponds to a first delivery period and the control circuit controls the first circuit to deliver the first therapy during a second delivery period substantially simultaneous with the recouping of the energy storage device and the charging circuit.

3. The device of claim 1, the control circuit further comprising:
   means for operating in a first mode to initiate transfer of the stored energy to the charging circuit during delivery of the first therapy;
   means for operating in a second mode to initiate transfer of the stored energy to the charging circuit subsequent to delivery of the first therapy; and
   means for transitioning between the first mode and the second mode based on predetermined criteria corresponding to the effectiveness of a previously-delivered first therapy.

4. The device of claim 3, wherein the predetermined criteria corresponds to a first parameter associated with a number of times the microprocessor redetects the predetermined event during the redetect period while operating in the second mode.

5. The device of claim 4, wherein the first parameter corresponds to a number of delivered sequences of the first therapy that do not terminate the predetermined event out of a total number of delivered sequences of the first therapy.

6. The device of claim 4, wherein the predetermined criteria corresponds to a second parameter associated with a number of times the microprocessor does not redetect the predetermined event during the redetect period while operating in the first mode.

7. The device of claim 6, wherein the second parameter corresponds to a number of delivered sequences of the first therapy that terminate the predetermined event out of a total number of delivered sequences of the first therapy.

8. The device of claim 6, wherein the microprocessor determines rhythms associated with the sensed signals, and wherein the control circuit includes means for utilizing different values for the first parameter and the second parameter, each of the values being respectively associated with a rhythm of the determined rhythms occurring during delivery of the first therapy.

9. The device of claim 3, further comprising a storage device coupled to the control circuit to store the predetermined criteria, wherein the predetermined criteria is programmably selected to be specific to a given patient.

10. The device of claim 3, wherein the microprocessor determines rhythms associated with the sensed signals and the predetermined criteria corresponds to a length of one or more of the determined rhythms.

11. The device of claim 3, wherein the microprocessor determines rhythms associated with the sensed signals and the control circuit transitions from the first mode to the second mode in response to a number of a predetermined rhythm of the determined rhythms being detected within a predetermined period of time.

12. The device of claim 3, wherein the predetermined criteria includes criteria associated with a change in a type of cardiac rhythm occurring prior to the delivery of the first therapy.

13. The device of claim 12, wherein the control circuit transitions from the second mode to the first mode in response to the criteria associated with a change in a type of cardiac rhythm occurring during the delivery of the first therapy.

14. The device of claim 3, wherein the control circuit transitions between the first mode and the second mode in response to a length of an episode corresponding to a delivered first therapy.

15. A method for delivering therapy in an implantable medical device, comprising:
   sensing cardiac signals;

detecting a predetermined event in response to the sensed signals;

delivering a first therapy, substantially simultaneous with coupling of a charging circuit and an energy storage device to generate a predetermined level of stored energy on the energy storage device, in response to the predetermined event being detected;

decoupling the charging circuit and energy storage device during a redetect period subsequent to delivery of the first therapy and prior to the predetermined level of the stored energy being generated on the energy storage device; and recoupling the energy storage device and the charging circuit in response to detecting the predetermined event during the redetect period.

16. The method of claim 15, wherein delivery of the first therapy corresponds to a first delivery period and further comprising delivering the first therapy during a second delivery period substantially simultaneous with the recoupling of the energy storage device and the charging circuit.

17. The method of claim 15, further comprising:
operating in a first mode to initiate generation of the stored energy by the charging circuit during delivery of the first therapy;
operating in a second mode to initiate generation of the stored energy by the charging circuit subsequent to delivery of the first therapy; and
transitioning between the first mode and the second mode based on predetermined criteria corresponding to the effectiveness of a previously-delivered first therapy.

18. The method of claim 17, wherein the predetermined criteria corresponds to a first parameter associated with a number of times the predetermined event is detected during the redetect period while operating in the second mode.

19. The method of claim 18, wherein the first parameter corresponds to a number of delivered sequences of the first therapy that do not terminate the predetermined event out of a total number of delivered sequences of the first therapy.

20. The method of claim 18, wherein the predetermined criteria corresponds to a second parameter associated with a number of times the predetermined event is detected during the redetect period while operating in the first mode.

21. The method of claim 20, wherein the second parameter corresponds to a number of delivered sequences of the first therapy that terminate the predetermined event out of a total number of delivered sequences of the first therapy.

22. The method of claim 20, further comprising:
determining rhythms associated with the sensed signals; and
utilizing different values for the first parameter and the second parameter, each of the values being respectively associated with a rhythm of the determined rhythms occurring during delivery of the first therapy.

23. The method of claim 17, wherein the predetermined criteria is programmably selected to be specific to a given patient.

24. The method of claim 17, further comprising determining rhythms associated with the sensed signals, wherein the predetermined criteria corresponds to a length of one or more of the determined rhythms.

25. The method of claim 17, further comprising determining rhythms associated with the sensed signals and transitioning from the first mode to the second mode in response to a number of a predetermined rhythm of the determined rhythms being detected within a predetermined period of time.

26. The method of claim 17, wherein the predetermined criteria includes criteria associated with a change in a type of cardiac rhythm occurring prior to the delivery of the first therapy.

27. The method of claim 26, further comprising transitioning from the second mode to the first mode in response to the criteria associated with a change in a type of cardiac rhythm occurring during the delivery of the first therapy.

28. The method of claim 17, further comprising transitioning between the first mode and the second mode in response to a length of an episode corresponding to the delivered first therapy.

29. A computer readable medium having computer executable instructions for performing a method comprising:
sensing cardiac signals;
detecting a predetermined event in response to the sensed signals;
delivering a first therapy, substantially simultaneous with coupling of a charging circuit and an energy storage device to generate a predetermined level of stored energy on the energy storage device, in response to the predetermined event being detected;
decoupling the charging circuit and energy storage device during a redetect period subsequent to delivery of the first therapy and prior to the predetermined level of the stored energy being generated on the energy storage device; and
recoupling the energy storage device and the charging circuit in response to detecting the predetermined event during the redetect period.

30. An implantable medical device, comprising:
means for sensing cardiac signals;
means for detecting a predetermined event in response to the sensed signals;
means for delivering a first therapy, substantially simultaneous with coupling of a charging circuit and an energy storage device to generate a predetermined level of stored energy on the energy storage device, in response to the predetermined event being detected;
means for decoupling the charging circuit and energy storage device during a redetect period subsequent to delivery of the first therapy and prior to the predetermined level of the stored enemy being generated on the energy storage device; and
means for recoupling the energy storage device and the charging circuit in response to detecting the predetermined event during the redetect period.

* * * * *

UNITED STATES PATENT AND TRADEMARK OFFICE
CERTIFICATE OF CORRECTION

PATENT NO. : 7,151,962 B2 Page 1 of 1
APPLICATION NO. : 10/835451
DATED : December 19, 2006
INVENTOR(S) : Paul A. Belk It is certified that error appears in the above-identified patent and that said Letters Patent is hereby corrected as shown below:

Column 15, line 56, please delete "enemy" and insert --energy--

Column 18, line 52, please delete "enemy" and insert --energy--

Signed and Sealed this

Fifteenth Day of May, 2007

JON W. DUDAS
*Director of the United States Patent and Trademark Office*